United States Patent [19]

Sibley et al.

[11] Patent Number: 5,429,922
[45] Date of Patent: Jul. 4, 1995

[54] COMPOSITION AND METHOD FOR DISTINGUISHING VIRULENT AND NON-VIRULENT TOXOPLASMA INFECTIONS

[75] Inventors: L. David Sibley, University City, Mo.; Roland Buelow; John C. Boothroyd, both of Palo Alto, Calif.

[73] Assignee: The Board of Trustees of the Leland Stanford Junior University, Stanford, Calif.

[21] Appl. No.: 755,009

[22] Filed: Sep. 5, 1991

Related U.S. Application Data

[63] Continuation-in-part of Ser. No. 616,693, Nov. 20, 1990, abandoned, which is a continuation of Ser. No. 166,384, Mar. 9, 1988, abandoned.

[51] Int. Cl.6 .............................................. C12Q 1/68
[52] U.S. Cl. ....................................... 435/6; 435/320.1; 536/23.1; 935/76; 935/77; 935/78
[58] Field of Search ................ 435/6, 320.1; 536/23.1; 935/76, 77, 78

[56] References Cited

PUBLICATIONS

Cameron et al., Parasitology 96:381–390 (1988).
McLaughlin et al., J. Clin. Microbiol., 26(9):1655–1658 (1988).
Gross et al., Infection and Immunology 59:4511–4516 (1991).
Bulow et al., J. Immunol. 147:3496–3500 (1991).
Christina et al., Parasitol. Res. 77:266–268 (1991).
Boothroyd et al., UCLA Symp. Mol. Cell. Biol. 42:237–250 (1987).
Kasper et al., J. Immunol. 130:2407 (1983).
Huynh et al., in "DNA Cloning" ed. Glover, vol. 1:94 (1985).
Johnson et al., Expt. parasit. 63:272–278 (1987).
Burg et al., J. Cell Biochem. 10A:145 (1986).
Burg et al., J. of Immunol. 144:3584–3591 (1988).

*Primary Examiner*—Jasemine C. Chambers

[57] ABSTRACT

Diagnostic assays based on the discovery of dimorphism in the p30 antigen and gene and the direct association of this dimorphism with the known bimodal virulence pattern. Assays can be based on different antigenic behavior of virulent (referred to here as type I) and avirulent (type II) p30 antigens or on the differences in the corresponding genes. There is a one-to-one relationship between the type I and type II antigen/genes and virulence. Specific genetic materials, specific antibodies, and analytical techniques that allow a diagnosis to be made between virulent and avirulent infections are disclosed.

5 Claims, 4 Drawing Sheets

FIG. 1A

```
       -150           -140           -130           -120           -110           -100
CAA TGT GCA CCT GTA GGA AGC TGT AGT CAC TGC TGA TTC TCG CTG TTC TCG GCA AGG GCT
                                                           A                       C

-90            -80            -70            -60            -50            -40
GAC GAC CGG AGT ACA GTT TTT GTG GGC AGA GCC GCT GTG CAG CTT TCC GTT GTT CTC GGT
                        T                                              C

-30            -20            -10             1             10             20
TGT GTC ACA TGT GTC ATT GTC GTG TAA ACA CAC GGT TGT ATG TCG GTT TCG CTG CAC CAC
                                                    Met Ser Val Ser Leu His His 30             40             50             60             70             80
TTC ATT ATT TCT GGT TTT TTG GCG AGT ATG TTT CCG AAG GCA GTG AGA CGC GCC GTC
Phe Ile Ile Ser Ser Gly Phe Leu Ala Ser Met Phe Pro Lys Ala Val Arg Arg Ala Val 90            100            110            120            130            140
ACG GCA GGG GTG TTT GCC GCG CCC ACA CTG ATG TCG TTC TTG CGA TGT GGC GCT ATG GCA
Thr Ala Gly Val Phe Ala Ala Pro Thr Leu Met Ser Phe Leu Arg Cys Gly Ala Met Ala
                                                                        T
                                                                        Val
```

```
             150                 160                 170                 180                 190                 200
TCG GAT CCC CCT CTT GTT GCC AAT CAA GTT GTC ACC TGC CCA GAT AAA AAA TCG ACA GCC
Ser Asp Pro Pro Leu Val Ala Asn Gln Val Val Thr Cys Pro Asp Lys Lys Ser Thr Ala 210                 220                 230                 240                 250                 260
GCG GTC ATT CTC ACA CCG GAG AAC CAC TTC ACT CTC AAG TGC CCT AAA ACA GCG CTC
Ala Val Ile Leu Thr Pro Thr Glu Asn His Phe Thr Leu Lys Cys Pro Lys Thr Ala Leu 270                 280                 290                 300                 310                 320
ACA GAG CCT CCC ACT CTT GCG TAC TCA CCC AAC AGG CAA ATC TGC CCA GCG GGT ACT ACA
Thr Glu Pro Pro Thr Leu Ala Tyr Ser Pro Asn Arg Gln Ile Cys Pro Ala Gly Thr Thr 330                 340                 350                 360                 370                 380
AGT AGC TGT ACA TCA AAG GCT GTA ACA TTG AGC TCC TTG ATT CCT GAA GCA GAA GAT AGC
Ser Ser Cys Thr Ser Lys Ala Val Thr Leu Ser Ser Leu Ile Pro Glu Ala Glu Asp Ser 390                 400                 410                 420                 430                 440
TGG TGG ACG GGG GAT TCT GCT AGT CTC GAC ACG GCA GGC ATC AAA CTC ACA GTT CCA ATC
Trp Trp Thr Gly Asp Ser Ala Ser Leu Asp Thr Ala Gly Ile Lys Leu Thr Val Pro Ile 450                 460                 470                 480                 490                 500
GAG AAG TTC CCC GTG ACA ACG CAG ACG TTT GTG GTC GGT TGC ATC AAG GGA GAC GAC GCA
Glu Lys Phe Pro Val Thr Thr Gln Thr Phe Val Val Gly Cys Ile Lys Gly Asp Asp Ala
```

```
          510            520            530            540            550            560
       CAG AGT TGT ATG GTC ACA GTA CAA GCC AGA GCC TCA TCG GTC AAT AAT GTC
                                G
       Gln Ser Cys Met Val Thr Val Gln Ala Arg Ala Ser Ser Val Val Asn Asn Val
                                     Thr 570            580            590            600            610            620
       GCA AGG TGC TCC TAC GGT GCA AAC AGC ACT CTT GGT CCT GTC AAG TTG TCT GCG GAA GGA
                                         G
       Ala Arg Cys Ser Tyr Gly Ala Asn Ser Thr Leu Gly Pro Val Lys Leu Ser Ala Glu Gly
                                         Asp 630            640            650            660            670            680
       CCC ACT ACA ATG ACC CTC GTG TGC GGG AAA GAT GGA GTC AAA GTT CCT CAA GAC AAC AAT
       Pro Thr Thr Met Thr Leu Val Cys Gly Lys Asp Gly Val Lys Val Pro Gln Asp Asn Asn 690            700            710            720            730            740
       CAG TAC TGT TCC GGG ACG ACG CTG ACT GGT TGC AAC GAG AAA TCG TTC AAA GAT ATT TTG
       Gln Tyr Cys Ser Gly Thr Thr Leu Thr Gly Cys Asn Glu Lys Ser Phe Lys Asp Ile Leu 750            760            770            780            790            800
       CCA AAA TTA AGT GAG AAC CCG TGG CAG GGT AAC GCT TCG AGT GAT AAT GGT GCC ACG CTA
                   C                                                 G
       Pro Lys Leu Ser Glu Asn Pro Trp Gln Gly Asn Ala Ser Ser Asp Asn Gly Ala Thr Leu
             Thr                                                       Lys
```

FIG. 1D

```
        810                 820                 830                 840                 850                 860
ACG ATC AAC AAG GAA GCA TTT CCA GCC GAG TCA AAA AGC GTC ATT ATT GGA TGC ACA GGG
         G
Thr Ile Asn Lys Glu Ala Phe Pro Ala Glu Ser Lys Ser Val Ile Ile Gly Cys Thr Gly
             Lys 870                 880                 890                 900                 910                 920
GGA TCG CCT GAG AAG CAT CAC TGT ACC GTG CAA CTG GAG TTT GCC GGG GCT GCA GGG TCA
                                         A
Gly Ser Pro Glu Lys His His Cys Thr Val Gln Leu Glu Phe Ala Gly Ala Ala Gly Ser
                                         Lys 930                 940                 950                 960                 970                 980
GCA AAA TCG TCT GCG GGA ACA GCC AGT CAC GTT TCC ATT TTC GCC ATG GTG ACC GGA CTT
                 G                                       T
Ala Lys Ser Ser Ala Gly Thr Ala Ser His Val Ser Ile Phe Ala Met Val Thr Gly Leu
                 Ala                                     Phe                     Ile 990                 1000                1010                1020
ATT GGC TCT ATC GCA GCT TGT GTC GCG TGA GTG ATT ACC GTT G

Ile Gly Ser Ile Ala Ala Cys Val Ala
```

COMPOSITION AND METHOD FOR DISTINGUISHING VIRULENT AND NON-VIRULENT TOXOPLASMA INFECTIONS

This invention was made with Government support under contract AI21423 awarded by the National Institutes of Health. The Government has certain rights in this invention.

This application is a continuation-in-part of U.S. application Ser. No. 07/616,693, filed Nov. 20, 1990, now abandoned, which is a continuation of U.S. application Ser. No. 07/166,384, filed Mar. 9, 1988, now abandoned.

BACKGROUND OF THE INVENTION

1. Field of the Invention

This invention relates to the field of disease diagnosis and also to the fields of genetic engineering and antibody production. More particularly it relates to the identification of virulent and non-virulent strains of Toxoplasma gondii by antibody binding and restriction fragment length polymorphism and to the preparation of compositions, particularly monoclonal antibodies, useful for such identification.

2. Description of the Background

Toxoplasmosis is caused by the protozoan parasite, Toxoplasma gondii. In humans, the disease is traditionally associated with the developing fetus in whom it can cause severe neurological problems manifesting as hydrocephaly, mental retardation and/or blindness [1, 2]. In healthy adults, the disease is typically mild, producing few if any symptoms. In immunocompromised adults, however, the parasite can cause severe or even fatal disease [3, 4, 5]. The disease also occurs in other mammals and is the leading cause of spontaneous abortion in sheep.

The parasite itself is extremely widespread and is typically acquired through the ingestion of undercooked meat in which tissue cysts containing the parasite may reside. Alternatively, the parasite can be contacted through ingestion of cat feces which contain the product of the complete sexual cycle, the oocyst. Both cyst forms are stable (the oocysts particularly so) and so avoidance of infection is difficult. In the U.S.A., serological studies indicate that about 15% of the population has had contact with the parasite [6]. In countries where eating lightly cooked meat is more common, this figure can rise to as much as 85% (e.g., in France [7]). The incidence of disease in the developing fetus is, fortunately, not as high as these figures might at first suggest because it appears that the fetuses of women who contract and control the disease prior to pregnancy are generally not at risk [8].

Diagnosis of congenital infection has in the past relied on serology (reviewed in [14]). This can be done postnatally or, ideally, pre-natally and relies on the relative titers of IgG and IgM (to deduce whether the titers are due to a current infection or legacy of a past infection). The factors contributing to the severity of disease in the developing fetus have been poorly understood. The only well-established factor is that the time of initial infection of the mother relative to conception is critical: infection significantly before conception such that an effective immune response has been mounted by the mother, results in little if any disease. Infection immediately before or after conception (i.e., in the first trimester of pregnancy) results in severe disease for the fetus of about 10–15% of fetuses. Infection late in pregnancy results in relatively less pathology, but occurs in a higher proportion of fetuses. It is unclear what determines whether a given fetus will or will not become diseased. The virulence of the parasite must, by definition, be a factor. Virulence is known to be bimodal, with all known strains of the parasite falling into two classes of relatively benign and highly virulent organisms. However, no simple assay for virulence was known. The direct measurement of virulence has been extremely difficult (requiring inoculation of mice with suspected samples and monitoring the mice for the appearance of the disease) and has not been implemented as part of the diagnostic armamentarium.

In the past two decades, toxoplasmosis has dramatically increased in a relatively new group of patients who are in some way immunodeficient as a result of post-transplantation therapy [5, 9, 10], neoplastic disease [11, 12, 13] or, most recently, acquired immunodeficiency syndrome (AIDS) [3, 4, 5]. In such immunodeficient patients, the parasite can cause a disseminated, potentially fatal form of the disease [5].

AIDS patients with toxoplasmosis typically first present with significant neuropathy (reviewed in [14]). This is due to the fact that one of the tissues most affected by the parasite is the brain wherein massive parasite cysts can be found. Infection is not limited to the brain, however, and tissue cysts can be found throughout the body [11]. The typical routine for diagnosis includes serology, computed tomography, magnetic resonance imaging and/or brain biopsy [1, 15, 16]. Of these, the only definitive route to diagnosis is the brain biopsy as this enables the direct visualization of the parasite, using immuno-peroxidase staining [17].

The course of treatment for toxoplasmosis in pregnant individuals is determined by the stage in pregnancy and whether the infection is acute or chronic. If infection is acute, spiromycin may be administered but is of unproven efficacy. More effective drugs such as combined therapy with pyrimethamine and sulfadiazine are not generally used because of their toxicity for the developing fetus. Hence, these latter drugs are employed in only rare cases where infection of the fetus (as opposed to the mother) is directly demonstrated. Such diagnosis has only been done on an experimental basis.

Treatment of toxoplasmosis in non-pregnant individuals is initiated and maintained with a drug regimen involving a combination of the folate antagonists, pyrimethamine and sulfadiazine [1, 14]. If the disease is identified soon enough, treatment is reasonably effective in combatting the acute disease. However, due to poor tolerance of the drugs, especially of the sulfa compounds in AIDS patients, maintenance on the drug therapy is frequently not possible and recrudescence of the infection is often observed (that is, the drug therapy reduces but does not eliminate the parasite infection).

Accordingly, there remains a need for the development of diagnostic assays that reliably detect and distinguish virulent toxoplasma infection from avirulent toxoplasma infection so that proper selection of a treatment regimen can occur.

LITERATURE CITED IN BACKGROUND SECTION

1. McCabe, R. E. and Remington, J. S. (1983). Eur. J. Clin. Micro. 2: 95–104.
2. Dubey, J. P. (1977). In J. P. Kreier (ed): Parasitic Protozoa. New York: Academic Press, pp. 101–237.

3. Gransden, W. R. and Brown, P. M. (1983). Brit. Med. J. 286: 6378.
4. Ensberger, W., Helm, E. B., Hopp, G., Stille, W. and Fischer, P.-.A. (1985). Deutsche Med. Wochenschrift 110: 83–86.
5. Luft, B. J., Brooks, R. G., Conley, F. K., McCabe, R. E. and Remington, J. S. (1984). JAMA 252: 913–917.
6. Feldman, H. A. (1965). Amer. J. Epidemiol. 81: 385–391.
7. Desmonts, G. and Couvreur, J. (1974). N. Engl. J. Med. 1110–1116.
8. Remington, J. S. and Desmonts, G. (1976). In J. S. Remington and J. O. Klein (eds): Infectious Diseases of the Fetus and Newborn Infant. Philadelphia: Saunders, p. 191.
9. Peacock, J. E. J.r., Folds, J., Orringer, E., Luft, B. and Cohen, M. S. (1983). Arch. Intern. Med. 143: 1235–1237.
10. Cohen, S. N. (1970). J. Am. Med. Assn. 211: 657–660.
11. Gleason, T. H. and Hamlin, W. B. (1974). Arch. Intern. Med. 134: 1059–1062.
12. Vietzke, W. M., Gelderman, A. H., Grimley, P. M. and Valsamis, M.P. (1968). Cancer 21: 816–827.
13. Frenkel, J. K., Nelson, B. M. and Arias-Stella, J. (1975). Hum. Path. 6:97–111.
14. Krahenbuhl, J. L. and Remington, J. S. (1982). In S. Cohen and K. S. Warren (eds): Immunology of Parasitic Infections. Oxford: Blackwell, pp. 356–421.
15. Cesbron, J. Y., Capron, A., Oviaque, G. and Santoro, F. (1985). J. Imm. Meth. 83: 151–158.
16. Erlich, H. A., Rodgers, G., Vaillancourt, P., Araujo, F. G. and Remington, J. S. (1983). Infect. Immun. 41: 683–690.
17. Conley, F. K., Jenkins, K. A. and Remington, J. S. (1981). Hum. Pathol. 12: 690–698.

SUMMARY OF THE INVENTION

The present invention provides diagnostic assays based on the discovery of dimorphism in the p30 antigen and gene and the direct association of this dimorphism with the known bimodal virulence pattern. Assays can be based on different antigenic behavior of virulent (referred to here as type I) and avirulent (also referred to as non-virulent; type II) p30 antigens or on the differences in the corresponding genes. There is a one-to-one relationship between the type I and type II antigen/genes and virulence. Specific genetic materials, specific antibodies, and analytical techniques that allow a diagnosis to be made between virulent and avirulent infections are disclosed in the following detailed description and examples.

BRIEF DESCRIPTION OF THE DRAWING

FIGS. 1A–1D presents the cDNA nucleic acid sequence (SEQ ID NO: 1) and deduced amino acid sequence (SEQ ID NO: 2) of the P30 gene from an avirulent strain and the cDNA nucleic acid sequence (SEQ ID NO: 3) and deduced amino acid sequence (SEQ ID NO: 4) of the P30 gene from a virulent strain RI-I. The RH sequences are identical to the avirulent sequences except where indicated. The underlined sequences at the beginning and the end of the sequences show respectively the oligonucleotides (sense and antisense) used in the PCR cloning. Numbering is from the first nucleotide of the first in-frame ATG codon. As the p30 protein is glycolipid-anchored, the C-terminal-most ten or more amino acids are almost certainly removed from the primary translation product.

DESCRIPTION OF SPECIFIC EMBODIMENTS

It has been discovered that Toxoplasma gondii isolates from around the world and from a variety of animal hosts fall into one of two distinct classes based on the following criteria:
1. virulence (as measured by LD50) in mice.
2. presence or absence of three polymorphic restriction sites (using the p30 surface antigen gene as probe).
3. ability to bind a monoclonal antibody specific for p30 of virulent strains.

There is a perfect correlation between all three phenomena such that the measurement of one accurately predicts the other two. Hence, the invention allows the extremely rapid determination of whether the strain responsible for any given clinical infection of animals or humans is virulent and thus informs the physician or veterinarian as to the likely outcome of the infection. This information is extremely important when deciding on the most effective course of therapy (i.e., in deciding to use the most effective but most toxic drugs over the less effective but safer alternatives).

The invention arose in the laboratories of the present inventors, where earlier studies had discovered genetic material encoding specific proteins of the protozoan parasite Toxoplasma gondii for the first time. One of these proteins was the p30 antigen. See U.S. application Ser. No. 07/616,693, filed Nov. 20, 1990, which is a continuation of U.S. application Ser. No. 07/166,384, filed Mar. 9, 1988, now abandoned, both of which are herein incorporated by reference. The p30 antigen is a major surface antigen (see Kasper et al., J. Imm. (1983) 130:2407–2412) and can be used for the production of vaccines or diagnostic standards (the latter for use in immunoassays for detecting T. gondii infections in general). However, there was no correlation between the p30 protein, p30 gene dimorphism, and virulence until the relationship was discovered by the present inventors.

FIG. 1 shows the coding for virulent and non-virulent p30 genes. The main DNA and amino acid sequence lines show the avirulent-strain sequence, with virulent-strain sequence differences being indicated on a separate line below the main sequence lines. The four sequences (specified and implied, from top to bottom) are referred to herein as SEQ. ID. NO. 1–4, respectively.

In general, the present invention is directed to any assay that detects the difference between type I and type II p30 antigens or between type I and type II p30 genes. In addition, assays based on the identification of antibodies in infected sera that show specific binding for one or the other but not both antigen types are also part of the invention. Since there is a one-to-one correlation between either of these differences and virulence, determination of virulence is now much easier than was possible previously using the mouse LD50 assay.

The manner in which the assay is carried out is immaterial to the invention. Many conventional assays can determine either differences between proteins or differences between genes or can determine the presence of specific antibodies in blood or other body fluids, and any of these conventional assays can be used in the present invention.

Turning first to assays based on differences in the antigens themselves, most such assays are based on differential binding of a protein (usually an antibody) with the two p30 types. Examples include both heterogeneous and homogeneous immunoassay techniques. Both techniques are based on the formation of an immunological complex between the binding protein and a corresponding specific antibody. Heterogeneous assays for p30 antigen typically use a specific monoclonal or polyclonal antibody bound to a solid surface. Sandwich assays are increasingly popular. Homogeneous assays, which are carried out in solution without the presence of a solid phase, can also be used, for example by determining the difference in enzyme activity brought on by binding of free antibody to an enzyme-antigen conjugate. A number of suitable assays are disclosed in U.S. Pat. Nos. 3,817,837, 4,006,360, 3,996,345.

The solid surface reagent in the above assay is prepared by known techniques for attaching protein material to solid support material, such as polymeric beads, dip sticks, or filter material. These attachment methods generally include non-specific adsorption of the protein to the support or covalent attachment of the protein, typically through a free amine group, to a chemically reactive group on the solid support, such as an activate carboxyl, hydroxyl, or aldehyde group.

In a second diagnostic configuration, known as a homogeneous assay, antibody binding to an analyte produces some change in the reaction medium which can be directly detected in the medium. Known general types of homogeneous assays proposed heretofore include (a) spin-labeled reporters, where antibody binding to the antigen is detected by a change in reported mobility (broadening of the spin splitting peaks), (b) fluorescent reporters, where binding is detected by a change in fluorescence efficiency, (c) enzyme reporters, where antibody binding effects enzyme/substrate interactions, and (d) liposome-bound reporters, where binding leads to liposome lysis and release of encapsulated reporter. The adaptation of these methods to the protein antigen of the present invention follows conventional methods for preparing homogeneous assay reagents.

In addition to the specific polypeptide sequences shown in Table 1, some peptide fragments based on these sequences and fragments representing minor variations thereof will have the binding activity of the various complete peptides and can be used in competitive binding assays that distinguish type I and type II p30 antigens. For example, fragments of the p30 peptide sequence that are capable of being recognized by immunoglobulins specific for the p30 antigen itself can readily be prepared and screened. Peptide synthesizers can be used to prepare small polypeptide fragments (e.g., less than 100 amino acids) or techniques of genetic engineering can be used to prepare larger fragments. A simple screening procedure that will identify suitable polypeptide fragments consists of preparing monoclonal antibodies to the appropriate p30 antigen, attaching the antibodies to an affinity column, and capturing peptide fragments that are retained by the bound antibody. Polyclonal antisera can be used instead of monoclonal antibodies if desired.

The ability to prepare and select appropriate immunologically active fragments from a larger protein is well known in the art and is described in a number of publications, including patents. See, for example, U.S. Pat. No. 4,629,783, which describes the preparation of immunologically active fragments of viral proteins.

One common variation is the preparation of a polypeptide of the invention in the form of a fused polypeptide. Such peptides are typically prepared by using the promoter region of a gene known to be expressed in a host and inserting nucleotides that encode all or a major portion of the amino acid sequence of the invention into the genetic sequence for the host protein. Such a fused protein has been prepared with $\beta$-galactosidase.

Another technique for preparing immunologically active peptide fragments is to synthesize a series of amino acids of from 5–100 amino acids in length (or any intervening length, such as 10, 15, or any other multiple of 2, 3, or 5 in this range) and screen for immunological activity using an antiserum (or monoclonal antibody). The fragments would be selected along the entire length of the peptide to optimize cross-reactivity (e.g., a series of peptides 20 amino acids in length and comprising $AA_1$–$AA_{20}$ $AA_5$–$AA_{25}$, $AA_{10}$–$AA_{30}$, etc.). The selected fragment would then correspond to particularly useful corresponding nucleotide sequences that could be used to produce large amounts of the peptide for use as described herein. In addition, minor variations of the previously mentioned peptides and DNA molecules are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid (i.e., a conservative replacement) will not have a major effect on the biological activity of the resulting molecule, especially if the replacement does not involve an amino acid at a binding site or other site of biologic activity. Whether a change results in a functioning peptide can readily be determined by direct analysis for function in an immunization or in a diagnostic test that relies on immunogenic specificity. Examples of this process are described later in detail. Peptides in which more than one replacement has taken place can readily be tested in the same manner. Preferred peptides differ at no more than 12, more preferably no more than 5, amino acids in any contiguous group of 20 amino acids. Standard conservative groups of amino acids are shown in parenthesis using the one-letter amino acid code: nonpolar (A,V,-L,I,P,M); aromatic (F,T,W); uncharged polar (G,S,T,C,N,Q); acidic (D,E); basic (K,R,H). The aromatic groups are sometimes considered to belong to the broader-defined nonpolar (F,W) or uncharged polar (T) groups.

Antibodies specific for p30 antigen are produced by immunizing an appropriate vertebrate host, e.g., rabbit, with purified p30 antigen or polypeptide derivatives of p30 antigen, by themselves or in conjunction with a conventional adjuvant. Usually, two or more immunizations will be involved, and blood or spleen will be harvested a few days after the last injection. For polyclonal antisera, the immunoglobulins can be precipitated, isolated and purified by a variety of standard techniques, including affinity purification using p30 antigen attached to a solid surface, such as a gel or beads in an affinity column. For monoclonal antibodies, the splenocytes normally will be fused with an immortalized lymphocyte, e.g., a myeloid cell line, under selective conditions for hybridoma formation. The hybridomas can then be cloned under limiting dilution conditions and their supernatants screened for antibodies having the desired specificity. Techniques for producing antibodies are well known in the literature and are exemplified by the publication *Antibodies: A Laboratory Manual* (1988) eds. Harlow and Lane, Cold Spring Harbor Laboratories Press, and U.S. Pat. Nos. 4,381,292, 4,451,570, and 4,618,577.

p30 antigen for use as immunogens in the preparation of anti-p30 antibodies (or in the assays in which natural specific antibodies for one of the antigen types is the target) can be readily purified from tissue or blood and its components, such as serum and plasma, taken from infected humans or animals and from cells genetically modified to produce p30 antigen or polypeptide derivatives thereof, by affinity chromatography using a monoclonal antibody specific for p30 antigen. In addition to the use of antibody affinity chromatography, p30 antigen and polypeptide derivatives thereof can be purified by a variety of other widely known protein purification techniques (either alone or in combination) including immunoprecipitation, gel filtration, ion exchange chromatography, chromatofocusing, isoelectric focusing, selective precipitation, electrophoresis, and the like. Derivatives having the desired immunogenicity can be prepared as described above.

p30 antigen, both glycosylated and unglycosylated, or polypeptide derivatives thereof, may be used for producing antibodies, either monoclonal or polyclonal, specific to p30 antigen. By polypeptide derivatives is meant polypeptides differing in length from natural p30 antigen and containing five or more amino acids from p30 antigen in the same primary order as found in p30 antigen as obtained from a natural source. Polypeptide molecules having substantially the same amino acid sequence as p30 antigen but possessing minor amino acid substitutions that do not substantially affect the ability of the p30 antigen polypeptide derivatives to interact with p30 antigen-specific molecules, such as antibodies, are within the definition of p30 antigen. Derivatives include glycosylated forms, aggregative conjugates with other p30 antigens molecules and covalent conjugates with unrelated chemical moieties. Covalent derivatives are prepared by linkage of functionalities to groups which are found in the p30 antigen amino acid chain or at the N- or C-terminal residue by means known in the art.

For both in vivo use of antibodies to p30 antigen and anti-idiotype antibodies and diagnostic use, it may be preferable to use monoclonal antibodies. Monoclonal antivirus particle antibodies or anti-idiotype antibodies can be produced as follows. The spleen or lymphocytes from an immunized animal are removed and immortalized or used to prepare hybridomas by methods known to those skilled in the art. To produce a human-human hybridoma, a human lymphocyte donor is selected. Epstein-Barr virus (EBV) can be used to immortalize human lymphocytes or a human fusion partner can be used to produce human-human hybridomas. Primary in vitro immunization with peptides can also be used in the generation of human monoclonal antibodies. Antibodies secreted by the immortalized cells are screened to determine the clones that secrete antibodies of the desired specificity.

Monoclonal antibodies against p30 have been prepared previously but not screened for the higher specificity required of the present invention. However, the screening technique is straightforward and easily carried out. An antibody composition (polyclonal or monoclonal) is prepared using either the type I or type II p30 antigen (from any strain) as an immunogen. After an initial screening to determine that the antibody composition actually binds with the immunogen, negative screening is carried out to select those antibody compositions that do not bind to the other member of the bimodal antigen pair. The resulting antibody compositions are capable of distinguishing between type I and type II p30 antigens and can be used in diagnostic techniques of the invention.

It may be easier in some case to carry out assays in which the target of the analysis is a specific antibody in the blood or other body fluid of an infected human or animal that shows the indicated specific binding for one but not both of the p30 antigen types. No purification, isolation, or handling of the parasite itself is then required. Numerous such assays exist (such as the tests now used for the AIDS antibody) and can be adapted to the present invention simply by substituting a type I or type II antigen (or any of the drerivatives or fragments discussed above that have the indicated specificity) for the antigen normally used in the assay. Because some anti-p30 antibodies will react with both types of antigens, a preferred assay would check for positive binding to one antigen type and negative binding to the other, particularly when using entire p30 molecules which have multiple determinants. When a small fragment is used that is known (by the screening process used to obtain the fragment) to bind only with a type-discriminating antibody, a single binding assay is preferred. Alternatively, a competitive binding assay can be used in which a labelled antibody standard known to discriminate between the two types competes with unknown antibody present in a sample. These examples of assays for type-specific anti-p30 antibodies are not intended to be exhaustive, but are merely examples of the many types of assays that could be used.

Assays of the invention can also be based on gene differences rather than antigen differences. Any conventional technique can be used. In most cases, amplification of the genetic material in the sample is desirable. One method for amplification of target nucleic acids, for later analysis by hybridization or other assays, is known as the polymerase chain reaction or PCR technique. The PCR technique can be applied to detecting p30 genes of the invention in suspected samples using oligonucleotide primers spaced apart from each other and based on the genetic sequence set forth herein. The primers are complementary to opposite strands of a double stranded DNA molecule and are typically separated by from about 50 to 450 nt or more (usually not more than 2000 nt). This method entails preparing the specific oligonucleotide primers and then repeated cycles of target DNA denaturation, primer binding, and extension with a DNA polymerase to obtain DNA fragments of the expected length based on the primer spacing. Extension products generated from one primer serve as additional target sequences for the other primer. The degree of amplification of a target sequence is controlled by the number of cycles that are performed and is theoretically calculated by the simple formula $2n$ where n is the number of cycles. Given that the average efficiency per cycle ranges from about 65% to 85%, 25 cycles produce from 0.3 to 4.8 million copies of the target sequence. The PCR method is described in a number of publications, including Saiki et al., Science (1985) 230:1350–1354; Saiki et al., Nature (1986) 324:163–166; and Scharf et al., Science (1986)

233:1076–1078. Also see U.S. Pat. Nos. 4,683,194; 4,683,195; and 4,683,202.

Oligonucleotide adaptors, probes, and sequencing and PCR primers can be synthesized by the phosphoramidite method with an Applied Biosystems (Foster City, Calif.) model 380A synthesizer, purified by polyacrylamide gel electrophoresis, and desalted on SEP-PAK $C_{18}$ cartridges (Waters; Milford, Mass.).

The PCR reactions can be performed according to the supplier of the PCR kit (Perkin/Elmer/Cetus) using the PCR primers described (see description of oligonucleotide synthesis).

Once the DNA is amplified, it can be analyzed by a variety of techniques that are used to detect differences between two different DNA sequences, such as restriction fragment length polymorphism (RFLP) analysis and selective hybridization. These techniques are well known and need not be described again in detail. However, they will be summarized here to indicate how the present invention is used with this known technology.

RFLP analysis relies on the ability of restriction endonucleases to generate DNA fragments of different length when two DNA molecules have a difference at the binding/cleavage site of the enzyme. In the assay, DNA obtained from samples is incubated with at least one restriction endonuclease that cleaves either the type I gene or the type II gene but not both. Other endonucleases can be used that cleave both types at common sites in order to cut the molecules in convenient lengths for analysis. Characteristic oligonucleotide fragments will be generated whose length depends on the type of p30 gene present. Analysis of the fragment lengths (usually on an electrophoresis gel) allows ready determination of which type p30 gene was present in the original sample, and thus ready determination of virulence.

Several gene differences that can be used in RFLP analysis are present in the p30 type I and type II genes. Comparison of the two sequences revealed that in the virulent p30 gene (type I SEQ ID NO: 2), there is a DdeI restriction endonuclease cleavage site (CTNAG, where N is any nucleotide) at position +753 and a Sau96I site (GGNCC) at position −98 that are not present in the avirulent (type II SEQ ID No: 1) gene due to single point mutations within the restriction site. Similarly, there is a HaeII site (RGCGCY, where R is either a G or an A and Y is either a C or a T) in the type II strain p30 genes (SEQ ID NO: 1) at position +131; this site is mutated in the type I strain (SEQ ID NO:2). Other differences can be used (or will become useful as more restriction endonucleases are discovered) as will be apparent to those skilled in the art.

Also contemplated is the identification of type I and type II p30 genes using oligonucleotide probes from the regions of variation of the two nucleotide sequences disclosed herein. Such probes will be relatively short because the differences between the sequences are minor, and long probes may not distinguish between the probes because the binding affinities are too similar. Probes at least 10, preferably at least 14, nucleotides in length, are desirable. Intermediate oligonucleotides up to 50, especially up to 20 or 30, nucleotides in length provide particularly specific and rapid-acting probes. Both RNA and DNA probes can be used. The hybridization conditions (especially temperature and salt concentration) are adjusted as necessary to provide differential hybridization.

In use, the probes are typically labelled in a detectable manner (e.g., with 32p, 3H, biotin, or avidin) and are incubated with single-stranded DNA or RNA from the organism in which a gene is being sought. Hybridization is detected by means of the label after single-stranded and double-stranded (hybridized) DNA (or DNA/RNA) have been separated (typically using nitrocellulose paper). Hybridization techniques suitable for use with oligonucleotides are well known.

Although probes are normally used with a detectable label that allows easy identification, unlabeled oligonucleotides are also useful, both as precursors of labeled probes and for use in methods that provide for direct detection of double-stranded DNA (or DNA/RNA), such as absorption onto nitrocellulose. Accordingly, the term "oligonucleotide probe" refers to both labeled and unlabeled forms.

Other techniques can be used to detect the differences between the type I and type II genes, as is known in the art.

Since various aspects of the invention require the use of genetic material, a brief discussion will be given of the preparation of genetic materials. However, this is not a key aspect of the present invention as all of the genetic materials can be isolated or otherwise prepared from publicly available sources using known techniques.

As the DNA sequence of the gene has been fully identified, it is possible to produce a virulent or avirulent p30 DNA gene entirely by synthetic chemistry, after which the gene can be inserted into any of the many available DNA vectors using known techniques of recombinant DNA technology. Thus the aspects of the present invention that require genetic material can be carried out using reagents, plasmids, and microorganism which are freely available and in the public domain at the time of filing of this patent application. However, it is preferred to prepare short oligonucleotide primers based on the identified sequence and to obtain the gene using the polymerase chain reaction (PCR) techniques using any of the many natural and readily available sources of T. gondii. See the examples below for a listing of specific sources.

For example, nucleotide sequences up to or even greater than 100 bases long can be readily synthesized on an Applied Biosystems Model 380A DNA Synthesizer as evidenced by commercial advertising of the same (e.g., Genetic Engineering News, November/December 1984, p. 3). Such oligonucleotides can readily be spliced using, among others, the technique of preparing overlapping complementary sequences (e.g, 1–100 of coding strand, 0–50 and 51–150 of complementary strand, 101–200 of coding strand, etc.) followed by hybridizing and ligating the strands.

Furthermore, automated equipment is also available that makes direct synthesis of any of the peptides disclosed herein readily available. In the same issue of Genetic Engineering News mentioned above, a commercially available automated peptide synthesizer having a coupling efficiency exceeding 99% is advertised (page 34). Such equipment provides ready access to the peptides of the invention, either by direct synthesis or by synthesis of a series of fragments that can be coupled using other known techniques.

Other DNA molecules that code for such peptides can readily be determined from standard lists of codons and are likewise contemplated as being equivalent to the DNA sequence of Table 1. In fact, since there is a fixed relationship between DNA codons and amino acids in a peptide, any discussion in this application of a replacement or other change in a peptide is equally applicable to the corresponding DNA sequence or to the DNA molecule, recombinant vector, or transformed microorganism in which the sequence is located (and vice versa).

In addition to the specific nucleotides listed in Table 1, DNA (or corresponding RNA) molecules of the invention can have additional nucleotides preceding or following those that are specifically listed. For example, poly A can be added to the 3'-terminal, short (e.g., fewer than 20 nucleotides) sequence can be added to either terminal to provide a terminal sequence corresponding to a restriction endonuclease site, stop codons can follow the peptide sequence to terminate translation, and the like. Additionally, DNA molecules containing a promoter region or other control region upstream from the gene can be produced. All DNA molecules containing the sequences of the invention will be useful for at least one purpose since all can minimally be fragmented to produce oligonucleotide probes or polymerase chain reaction (PCR) primers and be used in the isolation or detection of DNA from biological sources.

Although genes and corresponding proteins can be prepared by the totally synthetic techniques discussed above, in preferred embodiments of the invention genetic information is obtained from natural sources and identified as described herein, as previously mentioned. The genetic material is first obtained in the form of a gene library, using any of numerous existing techniques. The first of these is to randomly shear genomic DNA and insert this sheared material into expression vectors. If enough recombinants are generated, there is a good probability of having at least one recombinant in the population which is expressing a fusion protein corresponding to the antigen of interest. In practice, for a genome the size of T. gondii (about $7 \times 10^7$ bp), at least $5 \times 10^6$ independent recombinants are needed. This allows for the entire genome to be represented by recombinants where at least one insert will exist with one of its ends falling within any 10-base-pair region. Allowing for only 1 in 6 such insertions being in the correct orientation and reading frame, functional recombinants should exist in such a library with fusions corresponding to every 60 base pairs.

A clone obtained in the manner described above has been fully sequenced. This sequence was used to isolate other cDNA clones. Together, these sequences can be used to predict the complete protein-coding sequence of the gene as shown in Table 1. The primary translation product has a predicted Mr of 36,210 kD. It also has a probable hydrophobic signal peptide at its N-terminus, as expected for a surface antigen. It has one predicted N-glycosylation site (residue 267) consistent with investigations of previous workers which have indicated that the p30 protein may be a glycoprotein. Finally, it has a hydrophobic C-terminus which is not followed by any charged residues. This is apparently diagnostic of a process originally reported in trypanosomes whereby the hydrophobic polypeptide segment is replaced by a glycolipid anchor. Such a process is now known to occur for major surface antigens of Leishmania and Plasmodium as well.

The gene encoding the p30 antigen can be used for the production of full or modified peptides using standard techniques of manipulating and growing unicellular microorganisms. Antigens which are candidates for vaccine development and/or diagnostic reagents will include those recognized by serum from infected patients.

Although the techniques set forth above, when used in combination with the knowledge of those skilled in the art of genetic engineering and the previously stated guidelines, will readily enable isolation of the desired gene and its use in recombinant DNA vectors now that sufficient information is provided to locate the gene, other methods which lead to the same result are also known and may be used in the preparation of recombinant DNA vectors of this invention.

Expression of T. gondii protein can be enhanced by including multiple copies of the gene in a transformed host, by selecting a vector known to reproduce in the host, thereby producing large quantities of protein from exogenous inserted DNA (such as pUC8; ptac12; pIN ompA1, 2, or 3; pOTS; pAS1; or pKK223-3), or by any other known means of enhancing peptide expression.

In all cases, a T. gondii protein will be expressed when the DNA sequence is functionally inserted into the vector. By "functionally inserted" is meant in proper reading frame and orientation, as is well understood by those skilled in the art. Typically, a gene will be inserted downstream from a promoter and will be followed by a stop codon, although production as a hybrid protein (possibly followed by cleavage) may be used, if desired.

In addition to the above general procedures which can be used for preparing recombinant DNA molecules and transformed unicellular organisms in accordance with the practices of this invention, other known techniques and modifications thereof can be used in carrying out the practice of the invention. In particular, techniques relating to genetic engineering have recently undergone explosive growth and development. Many recent U.S. patents disclose plasmids, genetically engineering microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Patent 4,349,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified to the practice of the invention described in this specification by those skilled in the art of genetic engineering.

The techniques and reagents of the invention can be compiled into improved kits for the detection of Toxoplasmosis gondii, where the improvement allows virulent and non-virulent strains to be distinguished. Preferred kits will comprise a reagent selected from the group consisting of (1) for kits that determine the presence of T. gondii by the detection of specific nucleotide sequences, (a) restriction endonucleases that cleave either type I or type II p30 gene, but not both; (b) oligonucleotides that hybridize under the reaction conditions provided by the kit with either type I or type II p30 gene, but not both; and (c) antibodies that bind with either type I or type II p30 gene, but not both; and (2) for kits that determine the presence of T. gondii by the detection of a specific antigen binding event, specific binding molecules that bind either type I or type II p30 gene, but not both. Other kits can be prepared with other reagents that allow detection according to the general methods discussed above or in the examples below.

The standard meanings of words are given to words used in this specification. A preferred construction, however, is inherent in a number of the descriptive terms used in this specification. By "homogeneous" is meant, when referring to a peptide or DNA sequence, that the primary molecular structure (i.e., the sequence of amino acids or nucleotides) of substantially all molecules present in the composition under consideration is identical. The term "substantially" as used in the preceding sentence preferably means at least 95% by weight, more preferably at least 99% by weight, and most preferably at least 99.8% by weight. The presence of fragments derived from entire molecules of the homogeneous peptide or DNA sequence, if present in no more than 5% by weight, preferably 1% by weight, and more preferably 0.2% by weight, is not to be considered in determining homogeneity since the term "homogeneous" relates to the presence of entire molecules (and fragments thereof) have a single defined structure as opposed to mixtures in which several molecules of similar molecular weight are present but which differ in their primary molecular structure. The term "isolated" as used herein refers to pure peptide, DNA, or RNA separated from other peptides, DNAs, or RNAs, respectively, and being found in the presence of (if anything) only a solvent, buffer, ion or other component normally present in a biochemical solution of the same. "Isolated" does not encompass either natural materials in their native state or natural materials that have been separated into components (e.g., in an acrylamide gel) but not obtained either as pure substances or as solutions. The term "pure" as used herein preferably has the same numerical limits as "substantially" immediately above. The phrase "replaced by" or "replacement" as used herein does not necessarily refer to any action that must take place but to the peptide that exists when an indicated "replacement" amino acid is present in the same position as the amino acid indicated to be present in a different formula (e.g., when leucine is present at amino acid 3 of p30 instead of valine).

Salts of any of the peptides described herein will naturally occur when such peptides are present in (or isolated from) aqueous solutions of various pHs. All salts of peptides having the indicated biological activity are considered to be within the scope of the present invention. Examples include alkali, alkaline earth, and other metal salts of carboxylic acid residues, acid addition salts (e.g., HCl) of amino residues, and zwitter ions formed by reactions between carboxylic acid and amino residues within the same molecule.

The invention now being generally described, the same will be better understood by reference to the following examples which are provided for purposes of illustration only and are not to be considered limiting of the invention unless so specified.

EXAMPLE 1

The genetic and antigenic materials having the sequences set forth in Table 1 were isolated as described below.

Materials and Methods

A. Parasite Material

Most of the work described here uses the RH strain of Toxoplasma gondii which is the most commonly used laboratory strain amongst Toxoplasma researchers (Pfefferkorn et al., *Exp. Parasitol.* (1976) 39:365–376). It is highly virulent in animals and grows rapidly in culture making it ideal for obtaining large amounts of material. However, it has lost the ability to go through the complete sexual cycle in cats. Accordingly, more recent isolates, "C" and "P" strains which retain full biological function but are less virulent (Pfefferkorn et al., *J. Parasitol.* (1977) 63:158–159 and Ware et al., *Infect. Immun.* (1987) 55:778–783), were also used.

Parasites were generally grown in vitro in monolayers of cultured human foreskin fibroblasts (HFF). Typically, using the RH strain, infected cultures were maintained by seeding uninfected monolayers at about a 1:50 dilution every 48–72 hours. This yields about $10^9$ parasites from three T175 flasks of infected cultures. Parasites were harvested just as lysis occurred by passage of trypsinized cells through a syringe and removal of HFF debris by column chromatography, as described in Hoshino-Shimizu et al., J. Parasitol (1980) 66:989–991.

B. Gene Libraries

Three gene libraries for T. gondii were constructed in the inventors' laboratory. Unless otherwise noted, all libraries comprise λgt11 recombinants constructed by adding EcoRI linkers to methylated inserts and cloning into the EcoRI site of the vector. These are:

λkRHg1, a library of needle-sheared genomic DNA from RH strain.

2. CRHg1, a library of partially Sau3A digested RH genomic DNA inserted into the BamHI site of the cosmid vector c2XB (Bates et al., Gene (1983) 26:137146).

3. λRHc2, a cDNA library of RH strain tachyzoite mRNA prepared in the inventors' laboratory.

Libraries were constructed and manipulated as described in Huynh et al., In D. M. Glover (ed): DNA Cloning, Oxford: IRL Press (1985) pp. 49–78.

C. Antibodies

1. Monoclonal Anti-Toxoplasma

Monoclonal antibodies to p30 antigens of the RH strain of T. gondii were used in the initial isolation of genetic material. The 7B8 mAb against p30 (which does not distinguish type I from type II antigen) was reported earlier in Kasper et al., J. Imm. (1983) 130: 2407–2412.

A new monoclonal antibody (9B), specific for p30 of RH strain and thus for detection of virulence, is described below.

2. Polyclonal Anti-Toxoplasma

In addition to antisera raised by the inventors and others in the same laboratories, collaborators provided the following antisera:
  a. HC1 ... HC10: human sera from infants congenitally infected with T. gondii.
  b. HA: human sera from infected human adults.
  c. Rp30: rabbit antisera to purified p30 (prepared by immunoadsorption to mcAb 7B8).
  d. RTL1 and RTL2: rabbit antisera to lysates of T. gondii RH strain tachyzoites.

Results

A. Surface Antigen p30

Polyclonal antisera to p30 (Rp30) was used to screen a cDNA library, 1RHc2. Several recombinants were identified on the first screen, and of these, three were initially chosen for further examination based on the strength and reproducibility of the positive signal. The three recombinants were compared by isolating the inserts and using each as a hybridization probe against the other and in Southern blot analyses of digested genomic DNA. From this, it became clear that the three recombinants represent different genes, implying that at least two were due to fortuitous cross-reaction with the anti-p30 sera. Sequence and Southern blot analyses confirmed their distinct coding functions. To determine which was the true p30 gene, rabbit antisera was prepared to each fusion protein by excising the appropriate band from an acrylamide gel and injecting this into a rabbit. These sera were then used in Western blot analyses against a lysate of T. gondii. Only antisera to one clone, λTc30.5, showed reactivity to p30. This sera also showed reactivity to no other material in the lysate. That this was indeed p30, rather than a comigrating material, is evident from the reactivity of the antisera with purified p30. The other two clones are clearly distinct genes and presumably only fortuitously cross-reactive.

The λTc30.5 clone was fully sequenced and used to isolate other cDNA clones which have also been sequenced. From these, a complete sequence for the p30 coding region has been derived. The primary translation product has a predicted Mr of 36,210 kD. The identity of this gene as that encoding p30 was confirmed by sequencing of the purified protein, which established that the mature protein results from removal of a signal peptide. The p30 antigen also has a probable hydrophobic signal peptide at its N-terminus, as expected for a surface antigen. It has one predicted N-glycosylation site (residue 267) consistent with prior results indicating that p30 may be a glycoprotein. Finally, it has a hydrophobic C-terminus which is not followed by any charged residues. This is apparently diagnostic of the process originally reported in trypanosomes whereby the hydrophobic polypeptide segment is replaced by a glycolipid anchor. Such a process is now known to occur for major surface antigens of Leishmania and Plasmodium.

Using the predicted amino acid sequence, the sizes of cyanogen bromide fragments can be predicted. The data indicate two large fragments, one of which has a tyrosine. Using 125I-labeled p30, cyanogen bromide generates a single large fragment (by polyacrylamide gel electrophoresis) of the predicted size (11 kD) along with several small fragments. Moreover, the polypeptide sequence predicts substantial hydrophobicity for the protein as a whole as previously indicated for p30 by charge-shift immunoelectrophoresis. These results further confirm that the recombinant encodes p30.

The presumptive p30 gene is present in one copy per haploid genome and encodes a mRNA of 1.5 kb. Based on the signal intensity of the Northern analyses (the band is readily apparent in 0.25 hr) and abundance of cDNAs for this gene in the cDNA library (at least 20 plaques per 10,000 recombinant phage), it is an abundant message as would be expected of a protein present at about 3% of total cellular protein.

The P and C strain p30 genes were cloned using the polymerase chain reaction and oligonucleotides based on the RH strain sequence. Sequence analysis of the cloned product was by conventional technologies.

EXAMPLE 2

Twenty strains of Toxoplasma gondii have been analyzed with respect to the following properties: virulence, restriction-fragment length polymorphisms (RFLPs), and (for six of the twenty) antigenicity. These strains and their relative virulence are generally well known to those involved in the study of Toxoplasma but largely only with regard to the first parameter. These three parameters are discussed in more detail below.

1. Virulence.

Virulence is measured in mice as the number of parasites (tachyzoite form) which must be injected intraperitoneally in order to achieve killing of 100% of Balb/C mice (lethal dose or $LD_{100}$). Each of the twenty strains falls into one of two categories: those which have an $LD_{100}$ of less than ten organisms (termed "virulent") and those which have an $LD_{100}$ of over 1000 organisms (termed "avirulent"). The bimodality of this distribution (i.e., the fact that the relative virulence of the strains does not form a continuum) is well known.

2. RFLPs.

The gene encoding the major surface antigen, p30, has been cloned and sequenced from three strains. The first such sequence was for the virulent RH strain (Burg, J. L., Perelman, D., Kasper, L. H., Ware, P. L. and Boothroyd, J. C. 1988. Molecular analysis of the gene encoding the major surface antigen of Toxoplasma gondii. J. Immun. 141:3584–3591). Subsequently, the sequence of the p30 gene from two avirulent strains (P and C) was determined as reported here. Comparison of the two sequences revealed that in the p30 gene from RH, there is a DdeI restriction endonuclease cleavage site (CTNAG, where N is any nucleotide) at position +753 (numbering of Buelow and Boothroyd, 1991) and a Sau96I site (GGNCC) at position −98 that are not present in the P and C strains due to single point mutations within the restriction site. Similarly, there is a HaeII site (RGCGCY, where R is either a G or an A and Y is either a C or a T) in the P and C strain p30 genes at position +131; this site is mutated in the RH strain.

The remaining 17 strains were examined with regard to these three polymorphic sites. This was done by amplifying the p30 gene in vitro (using the polymerase chain reaction and a pair of oligonucleotides flanking the region containing these three polymorphic sites) followed by digestion with each of these three enzymes in turn. As shown in Tables 1 and 2, all avirulent strains had the same pattern of sites as P and C strains while all virulent strains were identical to the RH strain with respect to these three sites.

TABLE 1

PCR ANALYSIS OF HUMAN ISOLATES BASED ON p30 LOCUS

| Isolate | Location | DdeI | HaII | Sau961 | N/V |
|---|---|---|---|---|---|
| NON-AIDS ISOLATES: | | | | | |
| Tg51 | France | − | + | − | N |
| Tg68 | USA:CA | − | + | − | N |
| Tg96 | Australia | − | + | − | N |
| Tg132 | Japan | − | + | − | N |
| BEV | UK | − | + | − | N |
| RH-R | USA(JSR) | + | − | + | V |
| RH-88 | USA(ERP) | + | − | + | V |
| OH3 | Brazil | + | − | + | V |
| AIDS ISOLATES: | | | | | |
| HAR | USA | − | + | − | N |
| MOR | USA | + | − | + | V |
| SOL | USA | + | − | + | V |

N = nonvirulent
V = virulent

TABLE 2

PCR ANALYSIS OF ANIMAL ISOLATES BASED ON p30 LOCUS

| Isolate | Host | Location | DdeI | HaeII | Sau961 | N/V |
|---|---|---|---|---|---|---|
| ME49 | Sheep | USA:CA | − | + | − | N |
| PLK | Sheep | (ME49) | − | + | − | N |
| CEP | Cat | USA:NH | − | + | − | N |
| M7741 | Sheep | USA:IO | − | + | − | N |
| C56 | Chicken | USA:CA | − | + | − | N |
| Tg17 | Pig | Japan | − | + | − | N |
| GT1 | Goat | USA:MD | + | − | + | V |
| CT1 | Bovine | USA:MD | + | − | + | V |
| S11 | Pig | Brazil | + | − | + | V |

N = nonvirulent
V = virulent

3. Reactivity to a monoclonal antibody specific for p30.

A mouse hybridoma has been generated that produces a monoclonal antibody specific for p30 from RH strain Toxoplasma gondii. This was generated by injecting membrane fractions from RH strain parasites into mice, harvesting their spleens, generation of hybridomas by conventional means and screening of the resulting hybridomas for those secreting an antibody specific for p30. Preparation and screening is entirely conventional now that a virulence-determining factor (the p30 antigen) is known. The initial screening step was done by first examining the reactivity of the mAb by Western blot analysis in which whole lysates of T. gondii strain RH were resolved on a polyacrylamide gel, transferred to nitrocellulose and incubated in the presence of the supernatant from the many hybridomas, individually. Those mAbs that were believed to be specific for p30 based on their ability to react with a protein of the mobility known for p30 were further characterized. Confirmation that they were specific for p30 was based on demonstration that they react with a preparation of purified, homogeneous p30 from strain RH.

One such mAb reacted with p30 from strain RH but not with p30 from strains P and C. This mAb (9B2) was tested for its ability to react with five additional strains, being three virulent and two avirulent. All three virulent strains reacted with the mAb while both avirulent strains did not react with this mAb (Table 3 below).

4. Summary of experimental results

As shown by these examples, whether a strain is of the virulent or avirulent type can be assessed simply by determining whether it binds the 9B2 monoclonal antibody (or any antibody with the same virulence specificity) and/or whether it possesses one or other of the virulent-specific restriction sites.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

---

We claim:

1. A method of distinguishing virulent from non-virulent strains of Toxoplasma gondii, which comprises:
performing a restriction fragment length polymorphism assay to determine whether a p30 gene associated with said Toxoplasma gondii is type I or type II; and
identifying type I p30 as being indicative of a virulent Toxoplasma gondii infection and type II p30 as being indicative of non-virulent Toxoplasma gondii infection.

2. The method of claim 1, wherein said restriction fragment length polymorphism assay utilizes at least one restriction enzyme selected from the group consisting of HaeII, DdeI, and Sau96I.

3. The method of claim 1, wherein said restriction fragment length polymorphism assay is carried out on a sample obtained from a mammal suspected of being infected with Toxoplasma gondii.

4. The method of claim 3, wherein said mammal is a human or sheep.

5. The method of claim 1, which further comprises amplification of T. gondii DNA present in said sample prior to said restriction fragment length polymorphism assay.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1183 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 160..1170
        ( D ) OTHER INFORMATION: /codon_start=160
            / function="SURFACE ANTIGEN OF NON-VIRULENT T. GONDII STRAIN"
            / product="TYPE II P30 ANTIGEN"
            / gene="SAG1"
            / standard_name="P30"

( x i ) SEQUENCE DESCRIPTION: SEQ ID NO:1:

| | | | | | |
|---|---|---|---|---|---|
| CAATGTGCAC | CTGTAGGAAG | CTGTAGTCAC | TGCTGATTCT | CGCTGTTCTC | GGCAAGGGCT | 60 |
| GACGACCGGA | GTACAGTTTT | TGTGGGCAGA | GCCGCTGTGC | AGCTTTCCGT | TGTTCTCGGT | 120 |
| TGTGTCACAT | GTGTCATTGT | CGTGTAAACA | CACGGTTGT | ATG TCG GTT TCG CTG | | 174 |

```
                                                      Met  Ser  Val  Ser  Leu
                                                       1                    5

CAC  CAC  TTC  ATT  ATT  TCT  TCT  GGT  TTT  TTG  GCG  AGT  ATG  TTT  CCG  AAG    222
His  His  Phe  Ile  Ile  Ser  Ser  Gly  Phe  Leu  Ala  Ser  Met  Phe  Pro  Lys
                    10                  15                       20

GCA  GTG  AGA  CGC  GCC  GTC  ACG  GCA  GGG  GTG  TTT  GCC  GCG  CCC  ACA  CTG    270
Ala  Val  Arg  Arg  Ala  Val  Thr  Ala  Gly  Val  Phe  Ala  Ala  Pro  Thr  Leu
                25                  30                       35

ATG  TCG  TTC  TTG  CGA  TGT  GGC  GCT  ATG  GCA  TCG  GAT  CCC  CCT  CTT  GTT    318
Met  Ser  Phe  Leu  Arg  Cys  Gly  Ala  Met  Ala  Ser  Asp  Pro  Pro  Leu  Val
                40                  45                       50

GCC  AAT  CAA  GTT  GTC  ACC  TGC  CCA  GAT  AAA  AAA  TCG  ACA  GCC  GCG  GTC    366
Ala  Asn  Gln  Val  Val  Thr  Cys  Pro  Asp  Lys  Lys  Ser  Thr  Ala  Ala  Val
           55                  60                       65

ATT  CTC  ACA  CCG  ACG  GAG  AAC  CAC  TTC  ACT  CTC  AAG  TGC  CCT  AAA  ACA    414
Ile  Leu  Thr  Pro  Thr  Glu  Asn  His  Phe  Thr  Leu  Lys  Cys  Pro  Lys  Thr
 70                  75                  80                            85

GCG  CTC  ACA  GAG  CCT  CCC  ACT  CTT  GCG  TAC  TCA  CCC  AAC  AGG  CAA  ATC    462
Ala  Leu  Thr  Glu  Pro  Pro  Thr  Leu  Ala  Tyr  Ser  Pro  Asn  Arg  Gln  Ile
                90                  95                       100

TGC  CCA  GCG  GGT  ACT  ACA  AGT  AGC  TGT  ACA  TCA  AAG  GCT  GTA  ACA  TTG    510
Cys  Pro  Ala  Gly  Thr  Thr  Ser  Ser  Cys  Thr  Ser  Lys  Ala  Val  Thr  Leu
                105                 110                      115

AGC  TCC  TTG  ATT  CCT  GAA  GCA  GAA  GAT  AGC  TGG  TGG  ACG  GGG  GAT  TCT    558
Ser  Ser  Leu  Ile  Pro  Glu  Ala  Glu  Asp  Ser  Trp  Trp  Thr  Gly  Asp  Ser
                120                 125                      130

GCT  AGT  CTC  GAC  ACG  GCA  GGC  ATC  AAA  CTC  ACA  GTT  CCA  ATC  GAG  AAG    606
Ala  Ser  Leu  Asp  Thr  Ala  Gly  Ile  Lys  Leu  Thr  Val  Pro  Ile  Glu  Lys
     135                 140                      145

TTC  CCC  GTG  ACA  ACG  CAG  ACG  TTT  GTG  GTC  GGT  TGC  ATC  AAG  GGA  GAC    654
Phe  Pro  Val  Thr  Thr  Gln  Thr  Phe  Val  Val  Gly  Cys  Ile  Lys  Gly  Asp
150                  155                 160                      165

GAC  GCA  CAG  AGT  TGT  ATG  GTC  ACA  GTG  ACA  GTA  CAA  GCC  AGA  GCC  TCA    702
Asp  Ala  Gln  Ser  Cys  Met  Val  Thr  Val  Thr  Val  Gln  Ala  Arg  Ala  Ser
                170                 175                      180

TCG  GTC  GTC  AAT  AAT  GTC  GCA  AGG  TGC  TCC  TAC  GGT  GCA  AAC  AGC  ACT    750
Ser  Val  Val  Asn  Asn  Val  Ala  Arg  Cys  Ser  Tyr  Gly  Ala  Asn  Ser  Thr
                185                 190                      195

CTT  GGT  CCT  GTC  AAG  TTG  TCT  GCG  GAA  GGA  CCC  ACT  ACA  ATG  ACC  CTC    798
Leu  Gly  Pro  Val  Lys  Leu  Ser  Ala  Glu  Gly  Pro  Thr  Thr  Met  Thr  Leu
          200                 205                      210

GTG  TGC  GGG  AAA  GAT  GGA  GTC  AAA  GTT  CCT  CAA  GAC  AAC  AAT  CAG  TAC    846
Val  Cys  Gly  Lys  Asp  Gly  Val  Lys  Val  Pro  Gln  Asp  Asn  Asn  Gln  Tyr
     215                 220                      225

TGT  TCC  GGG  ACG  ACG  CTG  ACT  GGT  TGC  AAC  GAG  AAA  TCG  TTC  AAA  GAT    894
Cys  Ser  Gly  Thr  Thr  Leu  Thr  Gly  Cys  Asn  Glu  Lys  Ser  Phe  Lys  Asp
230                  235                 240                      245

ATT  TTG  CCA  AAA  TTA  AGT  GAG  AAC  CCG  TGG  CAG  GGT  AAC  GCT  TCG  AGT    942
Ile  Leu  Pro  Lys  Leu  Ser  Glu  Asn  Pro  Trp  Gln  Gly  Asn  Ala  Ser  Ser
                250                 255                      260

GAT  AAT  GGT  GCC  ACG  CTA  ACG  ATC  AAC  AAG  GAA  GCA  TTT  CCA  GCC  GAG    990
Asp  Asn  Gly  Ala  Thr  Leu  Thr  Ile  Asn  Lys  Glu  Ala  Phe  Pro  Ala  Glu
                265                 270                      275

TCA  AAA  AGC  GTC  ATT  ATT  GGA  TGC  ACA  GGG  GGA  TCG  CCT  GAG  AAG  CAT    1038
Ser  Lys  Ser  Val  Ile  Ile  Gly  Cys  Thr  Gly  Gly  Ser  Pro  Glu  Lys  His
          280                 285                      290
```

| | | | | | | | | | | | | | | | | |
|---|---|---|---|---|---|---|---|---|---|---|---|---|---|---|---|---|
| CAC | TGT | ACC | GTG | CAA | CTG | GAG | TTT | GCC | GGG | GCT | GCA | GGG | TCA | GCA | AAA | 1086 |
| His | Cys 295 | Thr | Val | Gln | Leu | Glu 300 | Phe | Ala | Gly | Ala | Ala 305 | Gly | Ser | Ala | Lys | |
| TCG | TCT | GCG | GGA | ACA | GCC | AGT | CAC | GTT | TCC | ATT | TTC | GCC | ATG | GTG | ACC | 1134 |
| Ser 310 | Ser | Ala | Gly | Thr | Ala 315 | Ser | His | Val | Ser 320 | Ile | Phe | Ala | Met | Val | Thr 325 | |
| GGA | CTT | ATT | GGC | TCT | ATC | GCA | GCT | TGT | GTC | GCG | TGAGTGATTA | | | CCGTTG | | 1183 |
| Gly | Leu | Ile | Gly | Ser 330 | Ile | Ala | Ala | Cys | Val 335 | Ala | | | | | | |

( 2 ) INFORMATION FOR SEQ ID NO:2:

( i ) SEQUENCE CHARACTERISTICS:
        ( A ) LENGTH: 1183 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( i x ) FEATURE:
        ( A ) NAME/KEY: CDS
        ( B ) LOCATION: 160..1170
        ( D ) OTHER INFORMATION: /codon_start=160
            / function="SURFACE ANTIGEN OF VIRULENT STRAIN"
            / product="TYPE I P30 ANTIGEN"
            / gene="SAG1"
            / standard_name="P30"

( x i ) SEQUENCE DESCRIPTION: SEQ ID NO:2:

| | | | | |
|---|---|---|---|---|
| CAATGTGCAC | CTGTAGGAAG | CTGTAGTCAC | TGCTGATTCT | CACTGTTCTC | GGCAAGGGCC | 60 |
| GACGACCGGA | GTACAGTTTT | TGTGGGCATA | GCCGCTGTGC | AGCTTCCCGT | TGTTCTCGGT | 120 |
| TGTGTCACAT | GTGTCATTGT | CGTGTAAACA | CACGGTTGT | ATG  TCG  GTT  TCG  CTG | | 174 |
| | | | | Met  Ser  Val  Ser  Leu | | |
| | | | | 1                     5 | | |

| | | | | | | | | | | | | | | | | |
|---|---|---|---|---|---|---|---|---|---|---|---|---|---|---|---|---|
| CAC | CAC | TTC | ATT | ATT | TCT | TCT | GGT | TTT | TTG | GCG | AGT | ATG | TTT | CCG | AAG | 222 |
| His | His | Phe | Ile | Ile 10 | Ser | Ser | Gly | Phe | Leu 15 | Ala | Ser | Met | Phe | Pro 20 | Lys | |
| GCA | GTG | AGA | CGC | GCC | GTC | ACG | GCA | GGG | GTG | TTT | GCC | GCG | CCC | ACA | CTG | 270 |
| Ala | Val | Arg | Arg 25 | Ala | Val | Thr | Ala | Gly 30 | Val | Phe | Ala | Ala | Pro 35 | Thr | Leu | |
| ATG | TCG | TTC | TTG | CGA | TGT | GGC | GTT | ATG | GCA | TCG | GAT | CCC | CCT | CTT | GTT | 318 |
| Met | Ser | Phe 40 | Leu | Arg | Cys | Gly | Val 45 | Met | Ala | Ser | Asp | Pro 50 | Pro | Leu | Val | |
| GCC | AAT | CAA | GTT | GTC | ACC | TGC | CCA | GAT | AAA | AAA | TCG | ACA | GCC | GCG | GTC | 366 |
| Ala | Asn | Gln | Val | Val 60 | Thr | Cys | Pro | Asp | Lys 65 | Lys | Ser | Thr | Ala | Ala | Val | |
| | Asn 55 | | | | | | | | | | | | | | | |
| ATT | CTC | ACA | CCG | ACG | GAG | AAC | CAC | TTC | ACT | CTC | AAG | TGC | CCT | AAA | ACA | 414 |
| Ile 70 | Leu | Thr | Pro | Thr | Glu 75 | Asn | His | Phe | Thr | Leu 80 | Lys | Cys | Pro | Lys | Thr 85 | |
| GCG | CTC | ACA | GAG | CCT | CCC | ACT | CTT | GCG | TAC | TCA | CCC | AAC | AGG | CAA | ATC | 462 |
| Ala | Leu | Thr | Glu | Pro 90 | Pro | Thr | Leu | Ala | Tyr 95 | Ser | Pro | Asn | Arg | Gln 100 | Ile | |
| TGC | CCA | GCG | GGT | ACT | ACA | AGT | AGC | TGT | ACA | TCA | AAG | GCT | GTA | ACA | TTG | 510 |
| Cys | Pro | Ala | Gly 105 | Thr | Thr | Ser | Ser | Cys 110 | Thr | Ser | Lys | Ala | Val 115 | Thr | Leu | |
| AGC | TCC | TTG | ATT | CCT | GAA | GCA | GAA | GAT | AGC | TGG | TGG | ACG | GGG | GAT | TCT | 558 |
| Ser | Ser | Leu 120 | Ile | Pro | Glu | Ala | Glu 125 | Asp | Ser | Trp | Trp | Thr 130 | Gly | Asp | Ser | |
| GCT | AGT | CTC | GAC | ACG | GCA | GGC | ATC | AAA | CTC | ACA | GTT | CCA | ATC | GAG | AAG | 606 |
| Ala | Ser 135 | Leu | Asp | Thr | Ala | Gly 140 | Ile | Lys | Leu | Thr | Val 145 | Pro | Ile | Glu | Lys | |

| | | | | | | | | | | | | | | | | |
|---|---|---|---|---|---|---|---|---|---|---|---|---|---|---|---|---|
| TTC | CCC | GTG | ACA | ACG | CAG | ACG | TTT | GTG | GTC | GGT | TGC | ATC | AAG | GGA | GAC | 654 |
| Phe 150 | Pro | Val | Thr | Thr | Gln 155 | Thr | Phe | Val | Val | Gly 160 | Cys | Ile | Lys | Gly | Asp 165 | |
| GAC | GCA | CAG | AGT | TGT | ATG | GTC | ACG | GTG | ACA | GTA | CAA | GCC | AGA | GCC | TCA | 702 |
| Asp | Ala | Gln | Ser | Cys 170 | Met | Val | Thr | Val | Thr 175 | Val | Gln | Ala | Arg | Ala 180 | Ser | |
| TCG | GTC | GTC | AAT | AAT | GTC | GCA | AGG | TGC | TCC | TAC | GGT | GCA | GAC | AGC | ACT | 750 |
| Ser | Val | Val | Asn 185 | Asn | Val | Ala | Arg | Cys 190 | Ser | Tyr | Gly | Ala | Asp 195 | Ser | Thr | |
| CTT | GGT | CCT | GTC | AAG | TTG | TCT | GCG | GAA | GGA | CCC | ACT | ACA | ATG | ACC | CTC | 798 |
| Leu | Gly | Pro 200 | Val | Lys | Leu | Ser | Ala 205 | Glu | Gly | Pro | Thr | Thr 210 | Met | Thr | Leu | |
| GTG | TGC | GGG | AAA | GAT | GGA | GTC | AAA | GTT | CCT | CAA | GAC | AAC | AAT | CAG | TAC | 846 |
| Val | Cys 215 | Gly | Lys | Asp | Gly | Val 220 | Lys | Val | Pro | Gln | Asp 225 | Asn | Asn | Gln | Tyr | |
| TGT | TCC | GGG | ACG | ACG | CTG | ACT | GGT | TGC | AAC | GAG | AAA | TCG | TTC | AAA | GAT | 894 |
| Cys 230 | Ser | Gly | Thr | Thr | Leu 235 | Thr | Gly | Cys | Asn | Glu 240 | Lys | Ser | Phe | Lys | Asp 245 | |
| ATT | TTG | CCA | AAA | TTA | ACT | GAG | AAC | CCG | TGG | CAG | GGT | AAC | GCT | TCG | AGT | 942 |
| Ile | Leu | Pro | Lys | Leu 250 | Thr | Glu | Asn | Pro | Trp 255 | Gln | Gly | Asn | Ala | Ser 260 | Ser | |
| GAT | AAG | GGT | GCC | ACG | CTA | ACG | ATC | AAG | AAG | GAA | GCA | TTT | CCA | GCC | GAG | 990 |
| Asp | Lys | Gly | Ala | Thr 265 | Leu | Thr | Ile | Lys | Lys 270 | Glu | Ala | Phe | Pro | Ala 275 | Glu | |
| TCA | AAA | AGC | GTC | ATT | ATT | GGA | TGC | ACA | GGG | GGA | TCG | CCT | GAG | AAG | CAT | 1038 |
| Ser | Lys | Ser 280 | Val | Ile | Ile | Gly | Cys 285 | Thr | Gly | Gly | Ser | Pro 290 | Glu | Lys | His | |
| CAC | TGT | ACC | GTG | AAA | CTG | GAG | TTT | GCC | GGG | GCT | GCA | GGG | TCA | GCA | AAA | 1086 |
| His | Cys 295 | Thr | Val | Lys | Leu | Glu 300 | Phe | Ala | Gly | Ala | Ala 305 | Gly | Ser | Ala | Lys | |
| TCG | GCT | GCG | GGA | ACA | GCC | AGT | CAC | GTT | TCC | ATT | TTT | GCC | ATG | GTG | ATC | 1134 |
| Ser 310 | Ala | Ala | Gly | Thr | Ala 315 | Ser | His | Val | Ser | Ile 320 | Phe | Ala | Met | Val | Ile 325 | |
| GGA | CTT | ATT | GGC | TCT | ATC | GCA | GCT | TGT | GTC | GCG | TGAGTGATTA | CCGTTG | | | | 1183 |
| Gly | Leu | Ile | Gly | Ser 330 | Ile | Ala | Ala | Cys | Val 335 | Ala | | | | | | |

( 2 ) INFORMATION FOR SEQ ID NO:3:

( i ) SEQUENCE CHARACTERISTICS:
( A ) LENGTH: 336 amino acids
( B ) TYPE: amino acid
( D ) TOPOLOGY: linear ( i i ) MOLECULE TYPE: protein ( i x ) FEATURE:
( D ) OTHER INFORMATION:
/ function="SURFACE ANTIGEN OF NON-VIRULENT T. GONDII STRAIN"
/ product="TYPE II P30 ANTIGEN"

( x i ) SEQUENCE DESCRIPTION: SEQ ID NO:3:

| | | | | | | | | | | | | | | | |
|---|---|---|---|---|---|---|---|---|---|---|---|---|---|---|---|
| Met 1 | Ser | Val | Ser | Leu 5 | His | His | Phe | Ile | Ile 10 | Ser | Ser | Gly | Phe | Leu 15 | Ala |
| Ser | Met | Phe | Pro 20 | Lys | Ala | Val | Arg | Arg 25 | Ala | Val | Thr | Ala | Gly 30 | Val | Phe |
| Ala | Ala | Pro 35 | Thr | Leu | Met | Ser | Phe 40 | Leu | Arg | Cys | Gly | Ala 45 | Met | Ala | Ser |
| Asp | Pro 50 | Pro | Leu | Val | Ala | Asn 55 | Gln | Val | Val | Thr | Cys 60 | Pro | Asp | Lys | Lys |
| Ser 65 | Thr | Ala | Ala | Val | Ile 70 | Leu | Thr | Pro | Thr | Glu 75 | Asn | His | Phe | Thr | Leu 80 |
| Lys | Cys | Pro | Lys | Thr | Ala | Leu | Thr | Glu | Pro | Pro | Thr | Leu | Ala | Tyr | Ser |

-continued

|   |   |   | 85 |   |   |   | 90 |   |   |   | 95 |   |
|---|---|---|---|---|---|---|---|---|---|---|---|---|
| Pro | Asn | Arg | Gln | Ile | Cys | Pro | Ala | Gly | Thr | Thr | Ser | Ser | Cys | Thr | Ser |
|   |   |   | 100 |   |   |   | 105 |   |   |   | 110 |   |

Pro Asn Arg Gln Ile Cys Pro Ala Gly Thr Thr Ser Ser Cys Thr Ser
          100             105            110

Lys Ala Val Thr Leu Ser Ser Leu Ile Pro Glu Ala Glu Asp Ser Trp
     115              120            125

Trp Thr Gly Asp Ser Ala Ser Leu Asp Thr Ala Gly Ile Lys Leu Thr
130               135            140

Val Pro Ile Glu Lys Phe Pro Val Thr Thr Gln Thr Phe Val Val Gly
145              150         155            160

Cys Ile Lys Gly Asp Asp Ala Gln Ser Cys Met Val Thr Val Thr Val
          165            170           175

Gln Ala Arg Ala Ser Ser Val Val Asn Asn Val Ala Arg Cys Ser Tyr
        180             185           190

Gly Ala Asn Ser Thr Leu Gly Pro Val Lys Leu Ser Ala Glu Gly Pro
     195              200            205

Thr Thr Met Thr Leu Val Cys Gly Lys Asp Gly Val Lys Val Pro Gln
210              215         220

Asp Asn Asn Gln Tyr Cys Ser Gly Thr Thr Leu Thr Gly Cys Asn Glu
225              230         235            240

Lys Ser Phe Lys Asp Ile Leu Pro Lys Leu Ser Glu Asn Pro Trp Gln
          245            250           255

Gly Asn Ala Ser Ser Asp Asn Gly Ala Thr Leu Thr Ile Asn Lys Glu
        260             265           270

Ala Phe Pro Ala Glu Ser Lys Ser Val Ile Ile Gly Cys Thr Gly Gly
     275              280            285

Ser Pro Glu Lys His His Cys Thr Val Gln Leu Glu Phe Ala Gly Ala
    290               295           300

Ala Gly Ser Ala Lys Ser Ser Ala Gly Thr Ala Ser His Val Ser Ile
305              310            315          320

Phe Ala Met Val Thr Gly Leu Ile Gly Ser Ile Ala Ala Cys Val Ala
             325            330           335

( 2 ) INFORMATION FOR SEQ ID NO:4:

( i ) SEQUENCE CHARACTERISTICS:
        ( A ) LENGTH: 336 amino acids
        ( B ) TYPE: amino acid
        ( D ) TOPOLOGY: linear ( i i ) MOLECULE TYPE: protein ( i x ) FEATURE:
        ( D ) OTHER INFORMATION:
            / function="SURFACE ANTIGEN OF VIRULENT T. GONDII STRAIN"
            / product="TYPE I P30 ANTIGEN"

( x i ) SEQUENCE DESCRIPTION: SEQ ID NO:4:

Met Ser Val Ser Leu His His Phe Ile Ile Ser Ser Gly Phe Leu Ala
1              5               10            15

Ser Met Phe Pro Lys Ala Val Arg Arg Ala Val Thr Ala Gly Val Phe
          20               25           30

Ala Ala Pro Thr Leu Met Ser Phe Leu Arg Cys Gly Val Met Ala Ser
        35             40            45

Asp Pro Pro Leu Val Ala Asn Gln Val Val Thr Cys Pro Asp Lys Lys
    50               55            60

Ser Thr Ala Ala Val Ile Leu Thr Pro Thr Glu Asn His Phe Thr Leu
65              70             75           80

Lys Cys Pro Lys Thr Ala Leu Thr Glu Pro Pro Thr Leu Ala Tyr Ser
          85              90           95

| | | | | | | | | | | | | | | |
|---|---|---|---|---|---|---|---|---|---|---|---|---|---|---|
| Pro | Asn | Arg | Gln 100 | Ile | Cys | Pro | Ala | Gly 105 | Thr | Thr | Ser | Ser | Cys 110 | Thr | Ser |
| Lys | Ala | Val 115 | Thr | Leu | Ser | Ser | Leu | Ile 120 | Pro | Glu | Ala | Glu 125 | Asp | Ser | Trp |
| Trp | Thr 130 | Gly | Asp | Ser | Ala | Ser 135 | Leu | Asp | Thr | Ala | Gly 140 | Ile | Lys | Leu | Thr |
| Val 145 | Pro | Ile | Glu | Lys | Phe 150 | Pro | Val | Thr | Thr | Gln 155 | Thr | Phe | Val | Val | Gly 160 |
| Cys | Ile | Lys | Gly | Asp 165 | Asp | Ala | Gln | Ser | Cys 170 | Met | Val | Thr | Val 175 | Thr | Val |
| Gln | Ala | Arg | Ala 180 | Ser | Ser | Val | Val | Asn 185 | Asn | Val | Ala | Arg | Cys 190 | Ser | Tyr |
| Gly | Ala | Asp 195 | Ser | Thr | Leu | Gly | Pro 200 | Val | Lys | Leu | Ser | Ala 205 | Glu | Gly | Pro |
| Thr | Thr 210 | Met | Thr | Leu | Val | Cys 215 | Gly | Lys | Asp | Gly | Val 220 | Lys | Val | Pro | Gln |
| Asp 225 | Asn | Asn | Gln | Tyr | Cys 230 | Ser | Gly | Thr | Thr | Leu 235 | Thr | Gly | Cys | Asn | Glu 240 |
| Lys | Ser | Phe | Lys | Asp 245 | Ile | Leu | Pro | Lys | Leu 250 | Thr | Glu | Asn | Pro | Trp 255 | Gln |
| Gly | Asn | Ala | Ser 260 | Ser | Asp | Lys | Gly | Ala 265 | Thr | Leu | Thr | Ile | Lys 270 | Lys | Glu |
| Ala | Phe | Pro 275 | Ala | Glu | Ser | Lys | Ser 280 | Val | Ile | Ile | Gly | Cys 285 | Thr | Gly | Gly |
| Ser | Pro 290 | Glu | Lys | His | His | Cys 295 | Thr | Val | Lys | Leu | Glu 300 | Phe | Ala | Gly | Ala |
| Ala 305 | Gly | Ser | Ala | Lys | Ser 310 | Ala | Ala | Gly | Thr | Ala 315 | Ser | His | Val | Ser | Ile 320 |
| Phe | Ala | Met | Val | Ile 325 | Gly | Leu | Ile | Gly | Ser 330 | Ile | Ala | Ala | Cys | Val 335 | Ala |